United States Patent
Gu et al.

(10) Patent No.: US 11,791,053 B2
(45) Date of Patent: Oct. 17, 2023

(54) METHOD AND SYSTEM FOR SIMULATING INTERVERTEBRAL DISC PATHOPHYSIOLOGY

(71) Applicant: SILICOSPINE INC., Miami, FL (US)

(72) Inventors: Weiyong Gu, Pinecrest, FL (US); Xin Gao, Miami, FL (US)

(73) Assignee: SILICOSPINE INC., Miami, FL (US)

( * ) Notice: Subject to any disclaimer, the term of this patent is extended or adjusted under 35 U.S.C. 154(b) by 78 days.

(21) Appl. No.: 16/891,844

(22) Filed: Jun. 3, 2020

(65) Prior Publication Data

US 2021/0012908 A1  Jan. 14, 2021

Related U.S. Application Data

(60) Provisional application No. 62/872,769, filed on Jul. 11, 2019.

(51) Int. Cl.
*G16H 50/50* (2018.01)
*G16H 70/60* (2018.01)
(Continued)

(52) U.S. Cl.
CPC .............. *G16H 50/50* (2018.01); *G06F 30/20* (2020.01); *G16H 15/00* (2018.01); *G16H 50/20* (2018.01);
(Continued)

(58) Field of Classification Search
CPC ........ G16H 50/50; G16H 15/00; G16H 50/20; G16H 50/30; G16H 70/60; G06F 30/20; G06F 2111/04; G06F 30/23
(Continued)

(56) References Cited

U.S. PATENT DOCUMENTS 7,121,832 B2  10/2006  Hsich et al.
7,133,546 B2  11/2006  Dehmeshki et al.
(Continued)

OTHER PUBLICATIONS

Gao, Verification of a Numerical Model for Simulating Intervertebral Disc Pathophysiology, 2020, Verification and Validation. vol. 83594. American Society of Mechanical Engineers (Year: 2020).*
(Continued)

*Primary Examiner* — Joshua B Blanchette
*Assistant Examiner* — Tran N Nguyen
(74) *Attorney, Agent, or Firm* — MALLOY & MALLOY, P.L.

(57) ABSTRACT

A computer-implemented method and system for modeling the pathophysiology of a human intervertebral disc may comprise an anatomic dataset and a biophysical model disposed in connection with a simulation program. The biophysical model may comprise a plurality of subsystems, including, without limitation, governing equations, constitutive equations, boundary conditions, initial conditions, and parameter values. By altering certain subsystems of the biophysical model, a user may selectively solve for certain pathophysiological metrics using at least one of a plurality of algorithms disposed within the simulation program. Moreover, such selective altering of the subsystems, such as, for instance, the boundary conditions, may allow a user to impose certain conditions on the computer-implemented method system, thereby allowing a user to dispose the intervertebral disc of the model at, for instance, in vivo human conditions, and subsequently initiate simulated degeneration conditions thereto, for the efficient and accurate modeling of such an intervertebral disc.

20 Claims, 7 Drawing Sheets

(51) Int. Cl.
  *G16H 15/00* (2018.01)
  *G16H 50/30* (2018.01)
  *G16H 50/20* (2018.01)
  *G06F 30/20* (2020.01)
  *G06F 111/04* (2020.01)

(52) U.S. Cl.
  CPC ............. *G16H 50/30* (2018.01); *G16H 70/60* (2018.01); *G06F 2111/04* (2020.01)

(58) Field of Classification Search
  USPC ........................................................ 705/2–3
  See application file for complete search history.

(56) References Cited

U.S. PATENT DOCUMENTS

| | | | |
|---|---|---|---|
| 8,491,655 B2 | 7/2013 | Adamo | |
| 8,825,131 B2 | 9/2014 | Peacock, III et al. | |
| 9,526,457 B2 | 12/2016 | Li et al. | |
| 9,724,013 B2 | 8/2017 | Peacock, III et al. | |
| 2007/0093998 A1 | 4/2007 | El-Baroudi | |
| 2010/0191071 A1* | 7/2010 | Anderson | G16H 20/00 600/301 |
| 2013/0053658 A1* | 2/2013 | Peacock | A61B 5/055 600/309 |
| 2013/0131486 A1 | 5/2013 | Copf et al. | |
| 2013/0197884 A1* | 8/2013 | Mansi | A61B 8/469 703/2 |
| 2015/0119688 A1 | 4/2015 | Peacock, III et al. | |
| 2016/0157751 A1* | 6/2016 | Mahfouz | A61B 6/12 600/409 |
| 2017/0252107 A1* | 9/2017 | Turner | G06N 5/04 |
| 2018/0055405 A1 | 3/2018 | Peacock, III et al. | |
| 2019/0214137 A1* | 7/2019 | Gupta | A61B 5/726 |
| 2020/0051340 A1* | 2/2020 | El Hajjar | G06T 15/04 |

OTHER PUBLICATIONS

Wan, Biphasic scaffold for annulus fibrosus tissue regeneration, 2008, Biomaterials 29.6: 643-652. (Year: 2008).*
Hadjipavlou, The pathophysiology of disc degeneration: a critical review, 2008, The Journal of bone and joint surgery. British vol. 90.10: 1261-1270. (Year: 2008).*
Wills, Simulating the sensitivity of cell nutritive environment to composition changes within the intervertebral disc, 2016, Journal of the Mechanics and Physics of Solids 90: 108-123 (Year: 2016).*
Dowdell, Intervertebral Disk Degeneration and Repair, 2017, Neurosurgery, Mar. 1;80(3S):S46-S54 (Year: 2017).*
Vadala, Intervertebral disc regeneration: from the degenerative cascade to molecular therapy and tissue engineering, 2015, J Tissue Eng Regen Med., Jun, 9(6):679-90 (Year: 2015).*

* cited by examiner

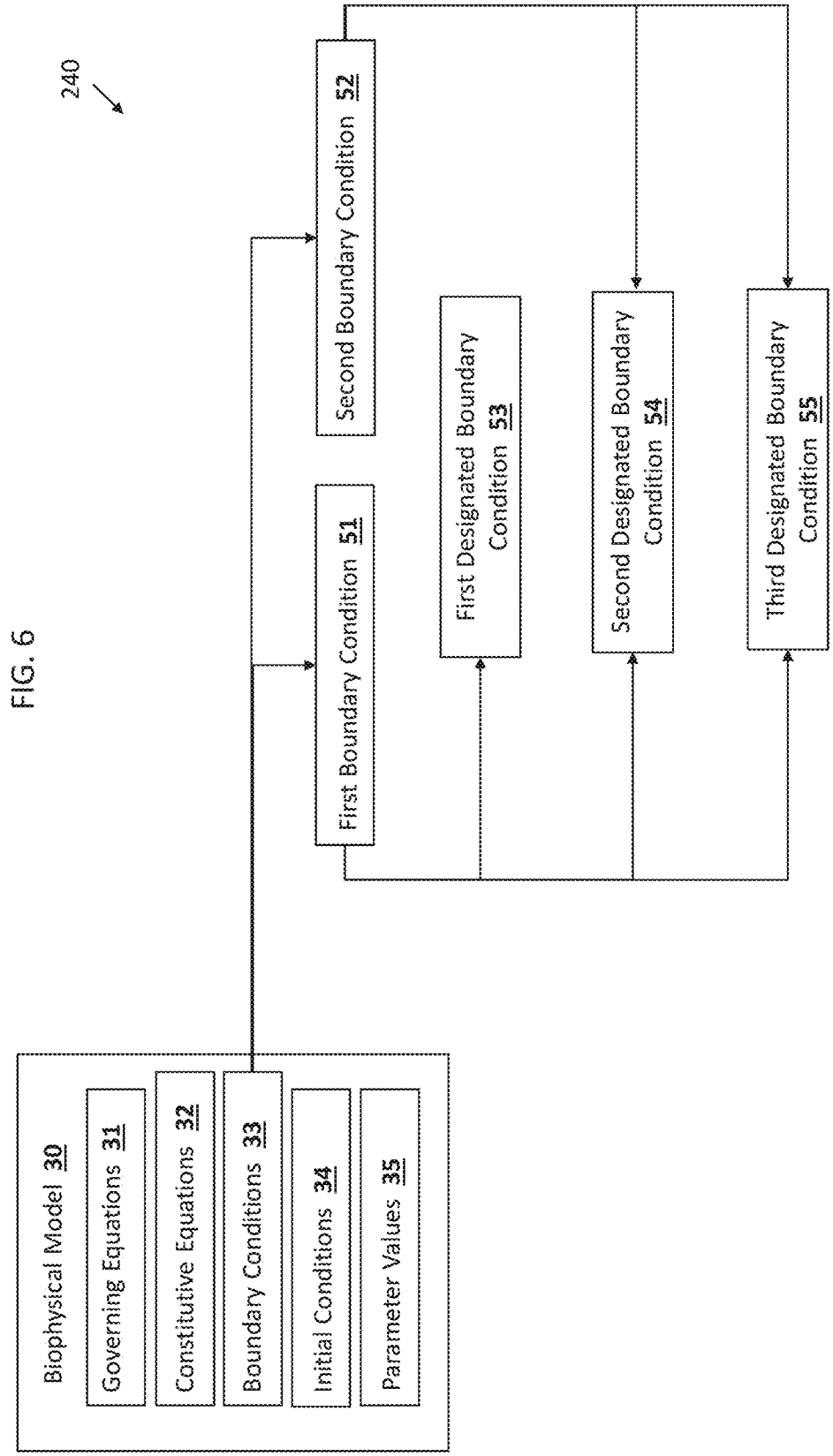

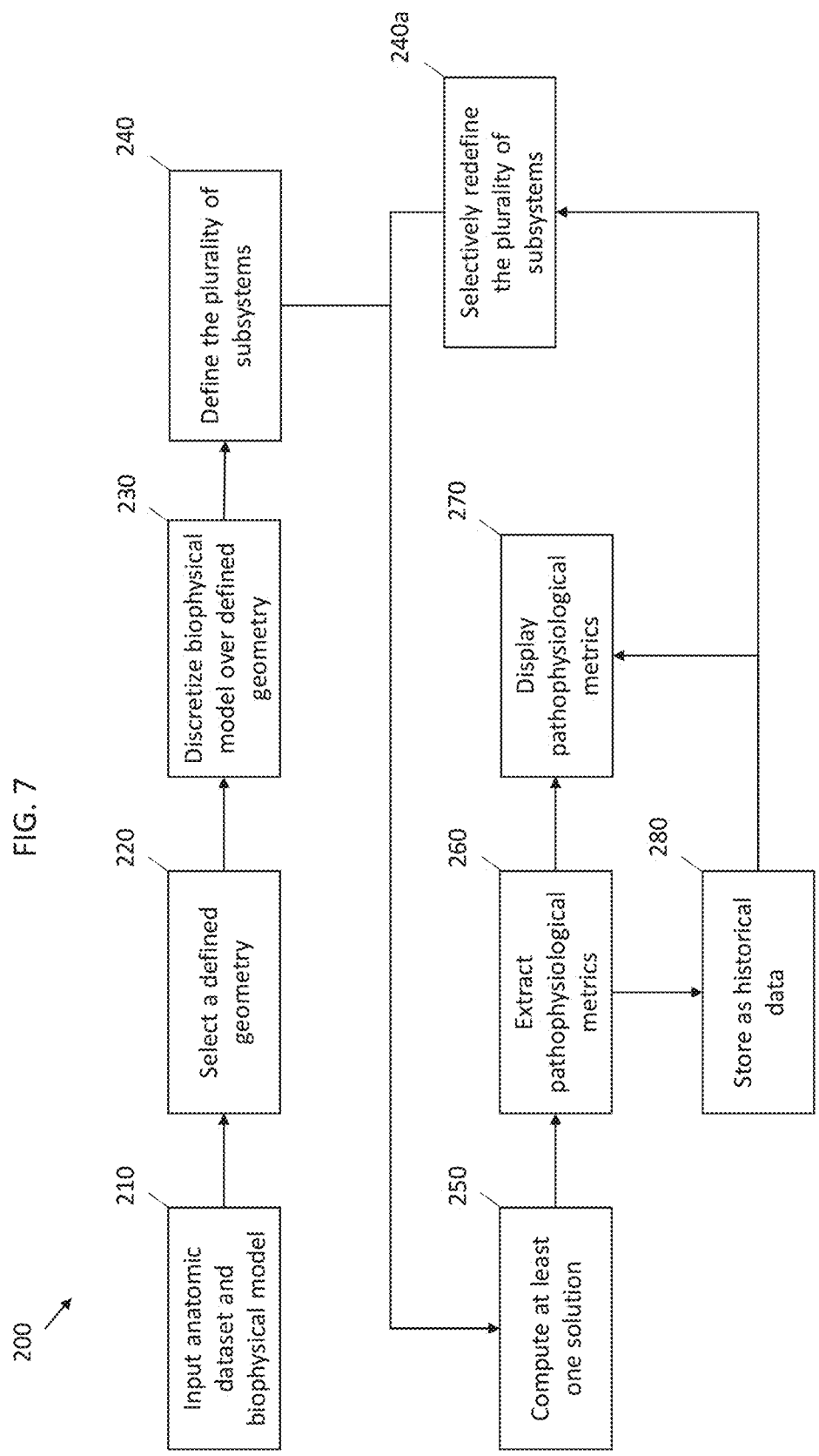

METHOD AND SYSTEM FOR SIMULATING INTERVERTEBRAL DISC PATHOPHYSIOLOGY

CLAIM OF PRIORITY

The present Non-Provisional patent application hereby makes a claim of priority to an earlier filed and U.S. provisional patent application having Ser. No. 62/872,769 and a filing date of Jul. 11, 2019, which is hereby incorporated herewith in its entirety.

BACKGROUND OF THE INVENTION

Field of the Invention

The present invention is directed to a method and system for simulating the pathophysiology of intervertebral discs including a computer-implemented program for implementing such simulation.

Description of the Related Art

An intervertebral disc is a fibrocartilaginous structure which lies between each of the vertebrae in the spinal column, functioning to both transfer loads and provide flexibility. Each intervertebral disc consists of a complex structure disposed in three distinct parts: (1) a fibrocartilaginous annulus fibrosus, comprising outer and inner regions and composed of concentrically orientated layers of fibrous tissue; (2) a central nucleus pulposus; and (3) two cartilaginous endplates. Each of these will be briefly discussed in greater detail hereafter.

The annulus fibrosus consists of a series of concentric rings, or lamellae, with aligned parallel collagen fibers disposed within each lamella, and elastic fibers disposed therebetween. Such a structural arrangement allows the annulus fibrosus to react to the tensile and compressive forces associated with spinal movement, thereby allowing an intervertebral disc to return to its original shape following such flexion and/or extension of the spine.

The nucleus pulposus comprises a gelatinous tissue composed primarily of proteoglycan aggrecan, with type II collagen fibers randomly arranged therein. Such an elastic structure disposed at the inner core of the intervertebral disc allows such intervertebral disc to withstand forces of compression and torsion, playing an essential role in the flexibility and stability of the spine.

The cartilaginous endplates are composed of osseous and hyaline-cartilaginous layers and are located between the vertebral endplates and the nucleus pulposus. Such cartilaginous endplates function to transmit compressive loads across the disc-bone interface, pressurize the nucleus pulposus, and support nutrient transport for the intervertebral disc.

As may be understood, degeneration of the intervertebral disc, which is associated with lower back pain, may significantly affect an individual's quality of life. Typically, degeneration of the intervertebral disc may alter various physiological aspects of the spine, such as the disk height of each intervertebral disc and the mechanics which stem therefrom, wherein such degeneration commonly leads to chronic segmental spinal instability. Specifically, as disk height decreases, the mechanics of the affected spinal segment is altered, which subsequently may lead to acceleration of the degeneration of adjacent spinal segments, as well as other spinal structures, such as small joints, ligaments, and muscles. Accordingly, as may be generally understood, the disruption in the normal architecture of any of the aforementioned structures from which the intervertebral disc is comprised, may lead to altered mechanics, and perhaps other physiological problems, such as disc herniation, a protrusion of the inner nucleus pulposus, or the application of pressure on the spinal cord or a nerve root.

It is generally understood cells play a significant role in the degeneration of intervertebral disc. Specifically, disc cells live in a complicated mechano-electrochemical environment, and their activities and viability are regulated by mechanical signals (e.g., deformation, stress, fluid flow, and solute transport), electrical signals (e.g., streaming potential and current), and biochemical signals (e.g., nutrition level, pH, and growth factor level). The cells function to maintain the balance between anabolism and catabolism of tissue; that is, they synthesize both the macromolecules, for the extracellular matrix maintenance, and the catabolic molecules, for the matrix breakdown. A detrimental tilt in this balance, due to the disturbance of the extracellular environment, may cause a cascade of biological reactions and result in the ruination of the matrix integrity and the failure in the tissue-level structure and function, thereby leading to tissue degeneration. Put simply, a lack of balance in the mechano-electrochemical environment in which such disc cells live may detrimentally affect the geometry of the intervertebral disc, and thereby lead to the degeneration of said intervertebral disc.

However, for a plurality of reasons, such as the asymptomatic nature of intervertebral disc degenerations, the understanding of the degeneration of intervertebral discs remains deficient. For instance, one such reason stems from a lack of understanding of the causes of such mechano-electrochemical imbalances. Specifically, as technology has progressed, the traditional thinking of such causes has shifted from the traditional views of environmental exposures, such as smoking, and occupation, to more contemporary views, such as mechanical, nutritional, and genetic factors.

Similarly, the current experimental methods and systems through which degeneration of intervertebral discs are studied compound such deficient understanding. Specifically, due to the difficulty of obtaining human spinal tissue, and particularly 'normal' human spinal tissue, the viability of conducting in vivo experiments is extremely limited. Accordingly, experimental model systems designed to study intervertebral disc degeneration normally consist of in vitro cell culture, in vitro explant culture of whole discs, and in vivo animal models.

Although these systems previously led to a significant amount of in-depth knowledge on the degenerative disc cascade, it may be understood these model systems are insufficient to infer the pathophysiology of human intervertebral discs and effective treatment strategies therefor. For instance, because in vitro experiments require highly specific conditions to induce the naturally observed behaviors of cells, and because different experiments on different cell cultures are often necessary to obtain different levels of understanding, it is challenging to systematically compile and analyze such experimental findings at multi-scale levels. Likewise, because in vitro experiments may only maintain near in vivo conditions for a short duration of time, it is challenging to investigate the chronic nature of the degeneration process, which may take decades, in such models. Finally, as may be understood, it is difficult to assess the efficacy of treatment strategies targeting the halting and reversal of the progression of intervertebral disc degeneration in animal models at least because the causes of disc degeneration are different. For instance, disc degeneration in animals is typically generated through surgery or chemical treatment, whereas disc degeneration in humans typically may occur from genetic factors and/or insufficient nutrient supply.

In view of the above challenges, there remains a need in the art for an improved model system designed to study the pathophysiology of human intervertebral discs. Given the complexity of the mechano-electrochemical environment in which intervertebral disc cells operate, computational model systems have proven particularly useful in the modeling thereof. Moreover, any such computational model system should be particularly disposed to study, through computational simulations, such intervertebral discs as a part of an in vivo human model, in addition to the in vitro cell, in vitro explant, and in vivo animal models present in prior art models. Further, such a computational model system should have the capacity to: (1) systematically synthesize existing experimental results and findings to illustrate intervertebral disc pathophysiology; (2) provide quantitative information on complicated interactions among the bioinformatics (e.g., biological, chemical, and mechanical) within the human intervertebral discs in various pathophysiological conditions; and (3) predict the evolution of disc pathophysiology caused by external stimuli, including factors causing disc diseases and interventions treating same, in an accurate and efficient manner.

SUMMARY OF THE INVENTION

The present invention is directed to a computer-implemented method and system for simulating the pathophysiology of intervertebral discs. At least one embodiment of the present invention includes an initial data input from any number of sources. Generally speaking, and after the input of such anatomic data, a simulation program may be implemented to utilize said anatomical data to solve sets of equations disposed within a biophysical model. Such sets of equations may include various combinations of governing equations, constitutive equations, boundary conditions, initial conditions, and parameter values. The equations disposed within such biophysical model may be solved by the simulation program according to a plurality of numerical methods, wherein the solutions to same may be displayed as a plurality of pathophysiological metrics.

Further, in at least one embodiment, such pathophysiological metrics may then be stored within the simulation program as historical data, for use as comparison values in subsequently enacted simulations. Moreover, as may be understood, such a biophysical model may be altered prior to running the simulation program, thereby allowing a user to obtain a variety of physiological metrics in accordance with a given intervertebral disc under a variety of different conditions. Accordingly, a user of such a computer-implemented method and system may not only obtain at least one of a plurality of physiological metrics in which he or she is interested in, but also may compare such physiological metric(s) with previously determined data, whether from the same intervertebral disc or data representing a sample population, thereby allowing for the effective use of such data for a variety of different purposes, including, without limitation, research, education, drug and medical device development, clinical trials, diagnoses, and treatment strategies.

In at least one embodiment of the present invention, the simulation of an intervertebral disc in the computer model envisioned herein begins with the aforementioned initial data input. As previously stated, such initial data input of an anatomic dataset may come from any number of sources, whether input manually by a user, or automatically from an interconnected medical imaging device or like apparatus. For instance, such an anatomic dataset may be manually input by a user in accordance with the results ascertained from a diagnostic test performed on a patient. Such a diagnostic test may comprise, for instance, the medical history of patient, a physical exam, and other more invasive procedures, such as a provocative discogram. Alternatively, the anatomic dataset may comprise information ascertained through various interconnected diagnostic imaging devices, such as X-rays, computed tomography scans, and magnetic resonance imaging scans, wherein such data may automatically be transmitted into, and received by, a memory disposed to receive the anatomic dataset. As may be understood, such an anatomic dataset may be stored by at least one memory device, for the later retrieval and use thereof. Moreover, as may be understood, such an anatomic dataset may be modified manually by a user for the tailoring towards any specific simulation of an intervertebral disc.

Moreover, in order to both provide greater flexibility in such a computer-implemented model, and to further provide greater efficiency in executing the simulation program disposed therein, such an anatomic dataset may comprise, at least, the geographic information of a given intervertebral disc. As may be understood, such geographic information may comprise, for instance, the disparate portions of an intervertebral disc, such as the annulus fibrosus, the central nucleus pulposus, and the two cartilaginous endplates, and the solid, fluid, and solute phases associated therewith.

In addition to such anatomic dataset, the memory may also store a biophysical model. Said biophysical model may comprise a system of mathematical equations expressing the complicated mechano-electrochemical environment in which the intervertebral disc operates. By way of a non-limiting example, a subsystem of the biophysical model may include governing equations, generally expressed through a plurality of differential equations, wherein said governing equations describe, for example, the spatiotemporal variations of variables representing the pathophysiological features of the intervertebral disc. Likewise, an additional subsystem, such as the constitutive equations, may describe the observed, theoretical, and/or assumed relationships between biophysical quantities, thereby characterizing specific features of the intervertebral disc. Additional subsystems may comprise initial conditions, parameter values, and boundary conditions, which may operate to constrain the simulation program to only those solutions which are the most efficient and reasonable. Further, as will be discussed later, such boundary conditions may further be disposed to define the type of simulation to be performed, whether an in vivo human model or otherwise. Moreover, it is envisioned each individual subsystem of said biophysical model may be situationally adjusted or modified, thereby providing greater flexibility to the simulation program.

In other words, and as will be discussed in greater detail hereafter, the biophysical model may be understood as a representation of the active and passive interaction between the various phases of an intervertebral disc, wherein at least a portion of the model comprises a mathematical description of the interactions between cells and all other constituents. Specifically, the biophysical model may be disposed to model intervertebral disc tissues as multiphasic materials, including, without limitation: (1) a solid phase, which is composed of multiple solid constituents including, without limitation, non-charged macromolecules, negatively charged glycosaminoglycans, and cells; (2) a fluid phase, including, without limitation, interstitial fluid; and (3) a solute phase comprising a plurality of species, such as, sodium ions, chloride anions, oxygen, glucose, lactate, etc.

Accordingly, such biophysical phases, and the biophysical activities occurring both therein and therewith, may be represented through the biophysical model using a plurality of theorems and principles, such as, without limitation, the continuum-mixture theory. For instance, constitutive equations comprising mass balance and linear momentum equations may be written for each phase, or any mixture thereof. Likewise, thermodynamics laws may be applied to constrain such constitutive equations.

Moreover, a plurality of assumptions may be made to further constrain the system, thereby simplifying same and increasing output efficiency. For instance, such assumptions may comprise, for instance: (1) the domain is fully saturated; (2) each phase is intrinsic incompressible; (3) the volume fraction of the solute phase is negligible; and (4) the changes in mass and volume of each phase due to biological activities is negligible.

With further reference to at least one embodiment of the present invention, a processor may be disposed in connection with the memory, wherein the processor is disposed to run a simulation program upon the input of the anatomical dataset and the biophysical model. Such a simulation program may comprise a plurality of algorithms, through which the solutions to said biophysical model may be ascertained. As may be understood, such algorithms may comprise, for instance, at least one of a plurality of applicable numerical methods including, without limitation, finite difference, finite volume, finite element, spectral, lattice Boltzmann, particle-based, level-set methods, and other past, present, or hereafter discover equivalents and/or combinations thereof. Accordingly, when a biophysical model over a specific anatomic dataset is solved, the simulation program may return the results as a series of pathophysiological datums in the form of discrete, numerical metrics.

As may be understood, such pathophysiological metrics may, in at least one embodiment of the present invention, be displayed in accordance with any number of visualization techniques through an interconnected graphical user interface, which may be disposed in input-output relation with the memory and the processor. Accordingly, such an interconnected graphical user interface may not only change the way in which such pathophysiological information is presented, but may also be disposed to modify any data disposed in the anatomical dataset, and any subsystems disposed in the biophysical model, upon user interaction, to specifically tailor the simulation program to any specific pathophysiological metric associated with a given intervertebral disc.

Further, in at least one embodiment of the present invention, the simulation obtained pathophysiological metrics may then be stored in a database to be compared with historical data obtained from alternative simulations, anatomic datasets, and/or biophysical models. The computer-implemented method may also include methods for manual or automatic analysis of the solutions to the biophysical model over the domain defined with the anatomic dataset. Comparison of the instant solutions with previously acquired solutions may subsequently be used to empirically create trends between different biophysical events and conditions, or to draw inferences about any level of disc health for diagnostic or prognostic analysis of intervertebral disc pathophysiology in relation to any external or internal factors.

These and other objects, features, and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 6 depicts a schematic representation in block-diagram form of a method for defining the plurality of subsystems in accordance with one embodiment of the present invention.

FIG. 7 depicts a schematic representation in block-diagram form of a method for simulating the pathophysiology of intervertebral discs in accordance with one embodiment of the present invention.

Like reference numerals refer to like parts throughout the several views of the drawings.

DETAILED DESCRIPTION OF THE PREFERRED EMBODIMENT

The present invention is directed towards a computer-implemented method and system for simulating the pathophysiology of intervertebral discs. Generally speaking, the present invention is directed towards at least one memory, which is disposed to store an anatomic database, a biophysical model, and a simulation program. The at least one memory may further be disposed in connection with at least one processor which may, upon user input, apply the simulation program to the anatomic database and the biophysical model to solve series of equations using at least one of a plurality of numerical methods to determine certain pathophysiological metrics associated with the given anatomic database. As may be understood, in at least one embodiment, the anatomic database and the biophysical model may be altered by a user to dispose the simulation thereof in various experimental models, such as in vivo human conditions, or to change other biophysical conditions, such as constitutive equations or initial conditions associated with the simulation model, to solve for pathophysiological metrics associated with an intervertebral disc disposed in varying degeneration conditions.

As previously stated, the present invention may utilize at least one memory disposed in connection with at least one processor, for effectuating the simulation of the pathophysiology of intervertebral discs. As may be understood, the at least memory may have computer-readable instructions stored thereon, and may comprise, for instance, solid state drives, RAM, hard disk drives, removable disk drives, network storage, data farms, cloud storage, and any other type of data storage reasonably suited for storing such computer-readable instructions, while taking into account the scale at which the simulation program of the present invention is disposed to operate. Such storage may be achieved entirely, or in part, by a sole computing device, which may be locally situated or otherwise. As may be further understood, in at least one embodiment of the present invention, the at least one memory and at least one processor may be further disposed in input/output connection with at least one graphic user interface, which may be disposed for user input directed towards the operation of the simulation program of the present invention.

Figure 1:
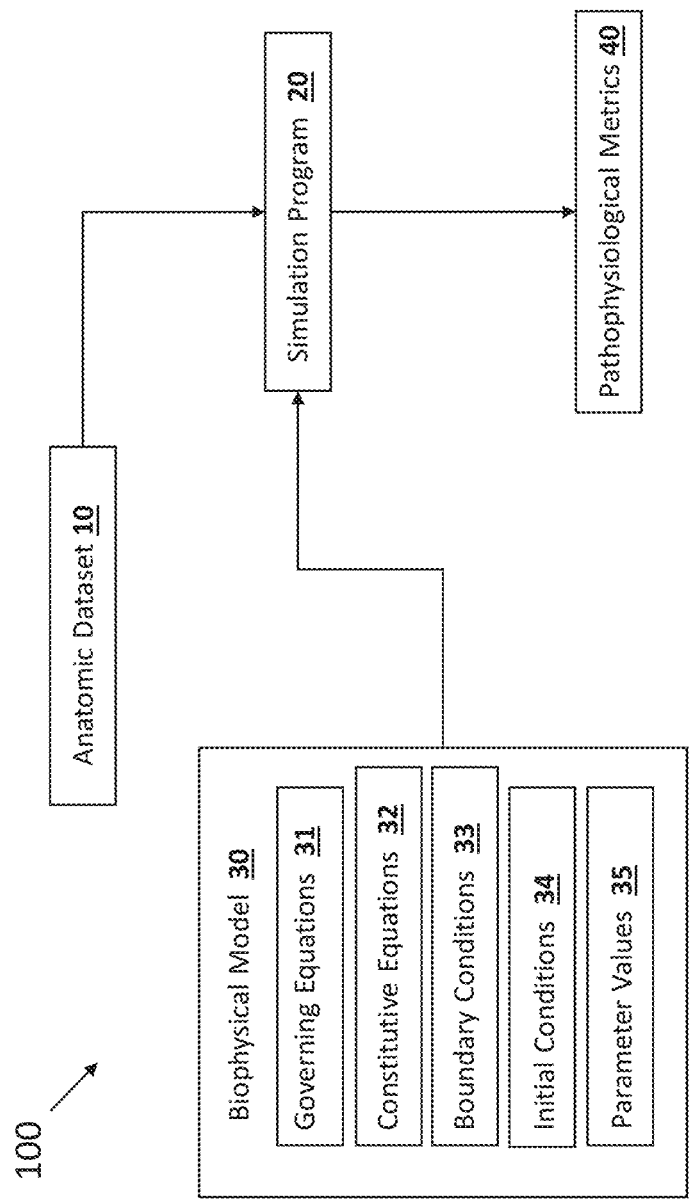
FIG. 1 depicts a schematic representation in block-diagram form of a method and system for simulating the pathophysiology of intervertebral discs according to one embodiment of the present invention.

Depicted in FIG. 1 is a schematic representation of a computer-implemented method and system for simulating the pathophysiology of intervertebral discs 100 in accordance with at least one embodiment of the present invention. As may be seen, disposed in connection with a simulation program 20, may be an anatomic dataset 10 and a biophysical model 30, which may comprise a plurality of subsystems, such as governing equations 31, constitutive equations 32, boundary conditions 33, initial conditions 34, and parameter values 35. As may be seen, the simulation program 20 may be disposed to determine the pathophysiological metrics 40 from the anatomic dataset 10 and the biophysical model 30.

Figure 2:
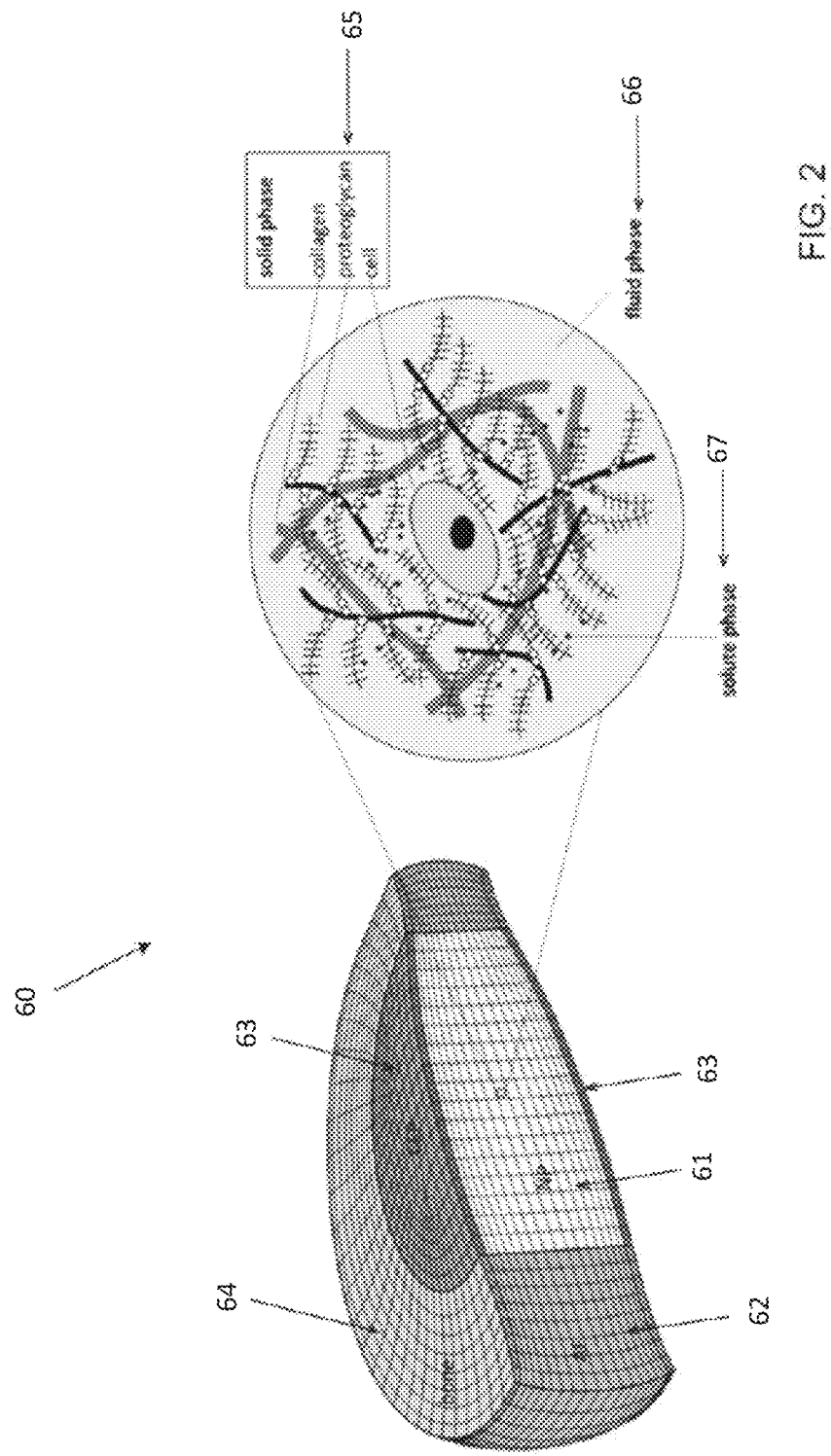
FIG. 2 depicts a schematic representation of the discrete components of an intervertebral disc to be simulated by a computer-implemented program according to one embodiment of the present invention.

With continued reference to FIG. 1, and with further reference to FIG. 2, it may be seen the anatomic dataset 10 may serve to represent a two-dimensional and/or three-dimensional intervertebral disc 60. For instance, the anatomic dataset 10 may comprise geometric information, such as the nucleus pulposus 61, the annulus fibrosis 62, and the cartilaginous endplates 63. Moreover, the anatomic dataset 10 may further comprise certain anatomic information about the intervertebral disc 60, such as the anatomic information pertaining to the solid phase 65, the fluid phase 66, and the solute phase 67 of the any particular geometric area of the anatomic dataset. For instance, the anatomic dataset 10 may further comprise a defined geometry 64, represented by the mesh disposed on the intervertebral disc 60, which may serve to specifically identify the geometric and anatomic information to which a given simulation pertains.

As may be understood, the anatomic dataset 10 may be generated from a variety of sources such as, for example, medical images of an intervertebral disc 60, as depicted in FIG. 2. Such medical images may be automatically disposed to be input into the computer-implemented method and system 100 of the present invention. For example, a medical imaging device or like apparatus, such as X-rays. computed topography scans, and magnetic resonance imaging scans, may be interconnected to the memory of the computer-implemented method and system 100 of the present invention, for the automatic upload of such anatomic information 10. Alternatively, users may elect to manually input the anatomic dataset 10 in accordance with any alternative medical or diagnostic tests performed on a patient. Such a diagnostic test may comprise, for instance, the medical history of the patient, a physical exam, and other more invasive procedures, such as a provocative discogram. Moreover, as may be understood, in at least one embodiment of the present invention, the anatomic dataset 10 may be manually modified by the user after the input into the memory thereof, for the tailoring towards any specific simulation of an intervertebral disc 60. For instance, the anatomic dataset 10 may be altered in subsequent simulations to obtain different sets of pathophysiological metrics from a given anatomic dataset 10.

As previously mentioned, and with further reference to FIG. 1, the memory may store a biophysical model 30, disposed to comprise a plurality of subsystems, which may comprise a system of mathematical equations expressing the complicated mechano-electrochemical environment in which the intervertebral disc operates. For example, as shown in FIGS. 1 and 2, an intervertebral disc 60 may be modeled as a mixture of multiple components, classified as the solid phase 65, fluid phase 66, and solute phase 67. The solid phase 65 may represent all the components, such as collagen, proteoglycan, and the cell, forming the solid matrix of an intervertebral disc 60. Likewise, the fluid phase 66 may represent interstitial fluid, whereas the solute phase 67 may represent all the solutes disposed in an intervertebral disc 60, such as sodium ions, chloride anions, oxygen, glucose, lactic acids, and growth factors. Accordingly, it may be assumed at any instant in time, all such phases of an intervertebral disc 60 are present at every material point. As may be understood, all such phases may be represented through the plurality of subsystems comprising the biophysical model 30, all of which will be discussed in greater detail hereafter.

One such subsystem of the biophysical model 30 comprises the governing equations 31. The governing equations 31 may describe the spatiotemporal variation of variables representing the pathophysiological features of the system and may be constructed for each component of an intervertebral disc 60 based on the biophysical principles inherent therein. For instance, the governing equations 31 may include, without limitation, equations detailing various conservation laws, such as the conservation of mass, the conservation of linear momentum, the conservation of angular momentum, and the conservation of energy, and laws pertaining to entropy inequality. Likewise, an electroneutrality condition may be applied through such governing equations 31.

As may be understood, the governing equations 31 may be typically expressed in the form of partial and/or ordinary differential equations, wherein combinations of such governing equations 31 may be used to model a particular biophysical model. For example, dependent upon the specified defined geometry 64 from the anatomic dataset 10, particular governing equations 31 may be applied to more accurately represent same. For instance, an electroneutrality condition may be used to accurately model various electrochemical effects, such as the differences between an area of interest and an environment. Likewise, because an imbalance of ions resulting between an electrochemical effect may drive water from one area of an intervertebral disc 60 to another, which may subsequently cause the swelling of tissues in the porous solid phase 65, additional governing equations 31 may be required to describe the space and temporal flow of such an intervertebral disc 60. Accordingly, combinations of governing equations 31 pertaining to such plurality of conservation laws may be necessary to provide a physical model of an intervertebral disc 60 compliant with the continuum-mixture theory. As may be understood, solutions to such governing equations 31 may be available for any given time or location of an intervertebral disc 60, despite such an intervertebral disc 60 having a variety of phases simultaneously present therein.

For example, for a domain consisting of a solid phase (s) 65 with multiple components ($\beta$), fluid phase (w) 66, and solute phase 67 with multiple species ($\alpha$), one may write governing equations 31 comprising the conservation equation of mass, conservation equation of linear momentum, and electroneutrality condition, all based on the continuum mixture theory, as follows:

$$\nabla \cdot \sigma = 0$$

$$\nabla \cdot (j^w + v^s) = 0$$

$$\frac{\partial(\phi^w c^\alpha)}{\partial t} + \nabla \cdot (j^\alpha + \phi^w c^\alpha v^s) = \phi^w \hat{c}^\alpha$$

$$\frac{\partial \rho^\beta}{\partial t} + \nabla \cdot (\rho^\beta v^s) = \hat{\rho}^\beta, \beta \in s$$

$$\sum_\alpha z^\alpha c^\alpha + z^F c^F = 0$$

where $\sigma$ is the total stress, $j^w$ is the fluid volume flux relative to the solid phase, $v^s$ is the velocity of the solid phase 65, $\phi^w$ is the volume fraction of the fluid phase 66, $c^\alpha$ is the concentration of solute species $\alpha$ (per fluid volume), t is time, $j^\alpha$ is the relative molar flux of solute species $\alpha$, $\hat{c}^\alpha$ represents consumption/production rate of solute species $\alpha$ (per unit volume), $\beta$ represents a component of the solid phase 65 (e.g., cell and glycosaminoglycan), $\rho^\beta$ is the mass density (or a quantity proportional to mass density) of $\beta$, $\hat{\rho}^\beta$ represents consumption/production rate of $\beta$, $z^\alpha$ is the valence of solute $\alpha$, $z^F$ and $c^F$ are the valence and concentration of charges attached to the solid phase 65, respectively.

As may be understood, the aforementioned governing equations 31 may be derived according to a plurality of assumptions, namely: (1) the domain is saturated; (2) each phase is intrinsic incompressible; (3) the volume fraction of the solute phase 67 is negligible; (4) the changes in mass and volume of the solute phase 67 and the fluid phase 66 due to biological activities are negligible; and (5) the effect of inertial forces on linear momentum in each phase is negligible (i.e., the system is at a quasi-static state).

With continued reference to FIGS. 1 and 2, it may be seen the biophysical model 30 may further include a subsystem comprising constitutive equations 32. Such constitutive equations 32 may comprise a plurality of equations disposed to quantitatively describe the relations between two or more biophysical quantities, thereby characterizing specific features on an intervertebral disc 60. As may be understood, such constitutive equations 32 may be derived from theory, observation, and assumption. For example, a constitutive equation 32 describing the glucose-concentration-level-dependent-cell-viability may be developed based on experimental observation and assumptions. Likewise, a constitutive equation 32 representing an external osmolarity-mechanical function may be developed in accordance with same. As may be understood, because constitutive equations 32 describing the relationships between two or more biophysical factors may be very complex and difficult to express for all solutions as an exact equation, such relationships may be approximated as models created according to historical empirical statistics for specific constraints.

For instance, and with the aforementioned governing equations 31 in mind, certain constitutive equations 32 may be written in accordance with the following examples. For example, where fluid is driven by the gradients of the modified fluid chemical potential ($\varepsilon^w$) and modified solute electro-chemical potential ($\varepsilon^\alpha$), a constitutive equations 32 directed thereto may be written as follows:

$$j^w = -RTk\left(\nabla \varepsilon^w + \sum_\alpha \frac{c^\alpha}{\varepsilon^\alpha} \nabla \varepsilon^\alpha H^\alpha\right)$$

where R is the universal gas constant, T is the absolute temperature, k is permeability, and $H^\alpha$ is the hindrance coefficient of solute species $\alpha$ for convection. Further, where solute is advected by fluid as well as driven by its electrochemical potential gradient, the solute flux can be written as:

$$j^\alpha = H^\alpha c^\alpha j^w - \frac{\phi^w c^\alpha d^\alpha}{\varepsilon^\alpha} \nabla \varepsilon^\alpha$$

where $d^\alpha$ is solute diffusivity. Here, the transport properties k, $d^\alpha$, and $H^\alpha$ can be constants or functions of other primary variables.

Further, the consumption/production rates, $\hat{c}^\alpha$ and $\hat{\rho}^\beta$, may be derived from biology principle, observation, and assumption. For example, based on biology principles, the rate of net mass change of glycosaminoglycan equals to the difference of synthesis rate and breakdown rate, and thus, such a constitutive equation 32 may comprise:

$$\hat{\rho}^\beta = \lambda_{syn}\rho^{cell} - \lambda_{degr}\rho^\beta, \beta = \text{glycosaminoglycan}$$

where $\lambda_{sys}$ is the glycosaminoglycan synthesis rate per unit cell, and $\lambda_{degr}$ is the glycosaminoglycan degradation rate per unit of glycosaminoglycan mass. As another example, a relationship between cell viability and extracellular glucose concentration ($c^g$) can be developed based on experimental observations as follows, $$\hat{\rho}^{cell} = m\left(\frac{c^g - c_0^g}{c^g + k_1} - \frac{|c^g - c_0^g|}{c^g + k_2}\right)$$

where m, $c_0^g$, $k_1$, and $k_2$ are parameters.

With further reference to FIG. 1, it may be seen boundary conditions 33 comprise another such subsystem of the biophysical model 30 and comprise constraints imposed thereon for the solution of such governing equations 31. As may be understood, such boundary conditions 33 may be adjusted according to the specific situation at hand, whether such situation pertains to the defined geometry 64 or otherwise. As may be understood, because the governing equations 31 typically comprise a plurality of partial and/or ordinary differential equations, and because solutions to such partial and/or ordinary differential equations typically comprise a plurality of solutions, of which only one may be reasonable, such boundary conditions 33 may be imposed upon the biophysical model 30 to eliminate such unreasonable solutions, thereby simplifying the model 100 and increasing the efficiency of the simulation thereof.

As may be understood, a plurality of boundary conditions 33 may be applied in accordance with the numerical methods in which the biophysical model 30 may be solved by the simulation program 20. As previously mentioned, such numerical methods may include, without limitation, finite difference, finite volume, finite element, spectral, lattice Boltzmann, particle-based, level-set methods, and other past, present, or hereafter discovered equivalents and/or combinations thereof. Accordingly, it may be understood such boundary conditions 33 may comprise any boundary condition suitable for the applicable numerical method used, and for constraining the biophysical model 30 in accordance with the disclosure herein.

However, in at least one embodiment of the present invention, such boundary conditions 33 may specifically comprise a first boundary condition 51, which may comprise a Neumann boundary condition, and a second boundary condition 52, which may comprise a Dirichlet boundary condition. As may be understood, such first boundary condition 51 and second boundary condition 52 may likewise comprise alternative boundary conditions which suitably constrain the biophysical model 30 in accordance with same.

As previously stated, the first boundary condition 51 may comprise a Neumann boundary condition. As may be understood, such a first boundary condition 51 may thus operate to specify the values in which the derivative of a solution may be applied within the boundary of the anatomic dataset 10. Likewise, the second boundary condition 52, which may comprise a Dirichlet boundary condition, may operate to specify the values a solution must take along the boundary of the anatomic dataset 10. The application of such first boundary condition 51 and such second boundary condition 52 will be discussed in greater detail hereafter.

Returning to FIG. 1, it may be seen a further subsystem of the biophysical model 30 may comprise the initial conditions 34. As may be understood, such initial conditions 34 may comprise the values of independent variables at some point in time, which may be designated as the initial time. Such initial conditions 34 may be constants and/or functions of other variables, such as, for instance, space. As may be understood, such initial conditions 34 may be adjusted in accordance with the simulation of a specified set of conditions of an intervertebral disc 60.

One final subsystem of the biophysical model 30, in accordance with at least one embodiment of the present invention, may comprise parameter values 35. Parameter values 35 may comprise numerical characteristics used to help define the remaining subsystems of the biophysical model 30, such as the constitutive equations 32, the boundary conditions 33, and the initial conditions 34. As may be understood, the values of such parameter values 35 may be obtained and/or estimated through experimental measurements.

With further reference to FIG. 1, at least one embodiment of the present invention may comprise a simulation program 20, disposed in connection with the anatomic dataset 10 and the biophysical model 30. Such a simulation program 20 may comprise, for instance, a numerical algorithm disposed to solve the biophysical model 30 over the domain defined by the anatomic dataset 10. As previously stated, such a numerical algorithm may comprise at least one of a plurality of numerical methods disposed to solve same, such as, for instance, finite difference, finite volume, finite element, spectral, lattice Boltzmann, particle-based, level-set methods, and other past, present, or hereafter discovered equivalents and/or combinations thereof. Accordingly, as may be understood, the application of certain numerical methods may be specifically applied to solve for specified pathophysiological metrics 40, in accordance with the biophysical model 30 and the domain defined by the anatomic dataset 10.

For example, a lattice Boltzmann method may be used to simulate fluid collision processes and viscous flow behavior of the fluid phase in the biophysical model. Likewise, finite difference methods may be used to solve simpler sets of linear equations, dependent upon the simplicity of the biophysical model 30. Level-set methods may be used to calculate interface interactions between two different fluids. For example, use of such level-set methods may be particularly useful in calculating the interactions between water-imbibed collagen in the solid phase and the interstitial fluid phase, because such fluid interfaces often have complicated tension and/or interaction effects due to the non-zero net force on the molecules at such fluid interface.

Accordingly, it is envisioned, in at least one embodiment of the present invention, any combination of such numerical methods may be tailored and applied to efficiently solve for any specific biophysical model 30. Thus, the method and system 100 in accordance with at least one embodiment of the present invention may be able to solve for, store, and analyze nearly any desired relationship between the biological, electrical, chemical, and mechanical events and/or interactions within an intervertebral disc 60 with just one anatomic dataset 10.

Figure 3:
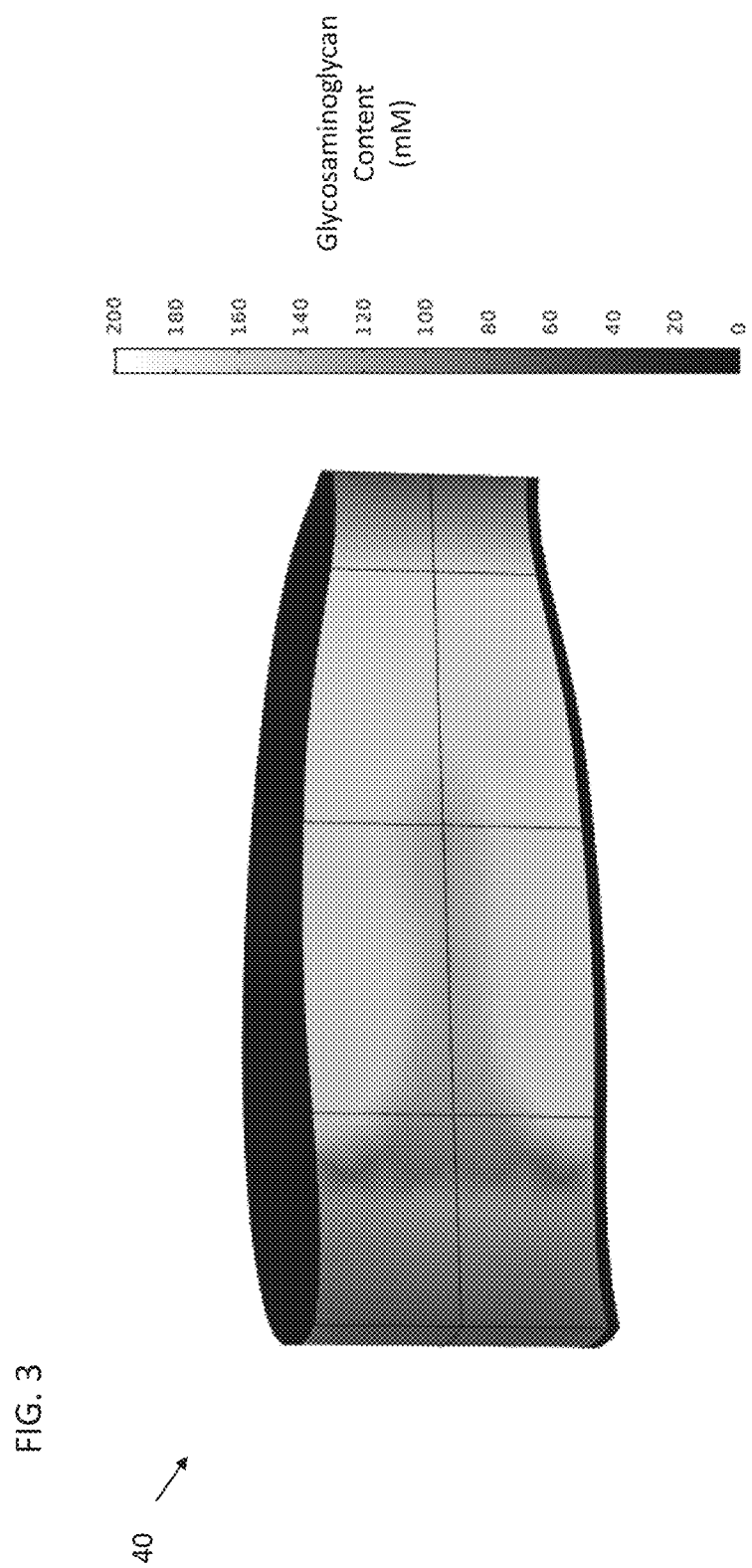
FIG. 3 depicts a schematic representation of the display of pathophysiological metrics in accordance with one embodiment of the present invention.
Figure 4:
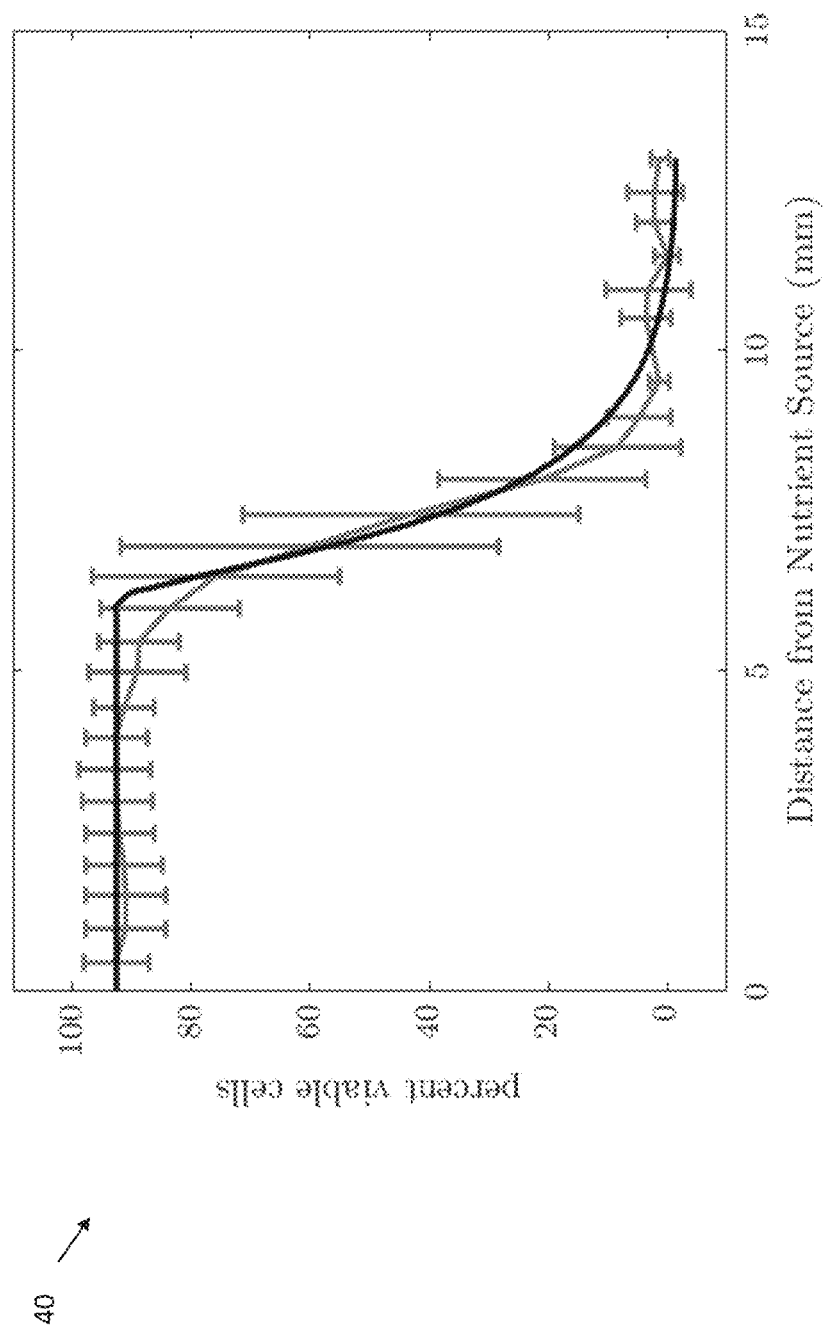
FIG. 4 depicts a schematic representation of the display of pathophysiological metrics in accordance with one embodiment of the present invention.

With further reference to FIG. 1, following the application of the simulation program 20, and the obtainment of solutions to the biophysical model 30, it may be understood pathophysiological metrics 40 may be extracted therefrom. Such pathophysiological metrics 40 may subsequently be displayed in accordance with any number of visualization techniques through a graphic user interface, as previously mentioned. For example, such pathophysiological metrics 40 may be used to illustrate the simulation of disc degeneration caused by the reduction of permeability of the cartilaginous endplates, as depicted in FIG. 3, wherein the glycosaminoglycan content is represented by the concentration of charged groups attached thereto. Likewise, such pathophysiological metrics 40 may be used to illustrate the spatial distribution of cell viability in an engineered intervertebral disc tissue, as depicted in FIG. 4, wherein the black line represents the pathophysiological metrics 40 and the gray line represents experimental measurements.

Such pathophysiological metrics 40 may have a variety of uses. For instance, such pathophysiological metrics 40 may be used as data collection for the systematic synthetization and creation of a more accurate illustration of intervertebral disc pathophysiology. Moreover, in at least one embodiment, such pathophysiological metrics 40 may be stored in the memory as historical data, for the subsequent comparison with pathophysiological metrics 40 derived from subsequent simulations. As may be understood, such comparison may be accomplished in any number of ways, whether through direct eye-test comparisons, or through further statistical models and/or analysis, such as the provision of normal distribution ranges and comparison of percentile ranges. Accordingly, the pathophysiological metrics 40 may be used to draw inferences in accordance with such historical data or may simply be incorporated as another data point in a trend analysis. Thus, comparison with such historical data may provide for the determination of any differences and/or similarities between intervertebral discs, anatomic dataset, and/or simulations, which may accordingly be used in the prediction of the evolution of the pathophysiology of an intervertebral disc, and for prognostic and diagnostic information thereto.

Figure 5:
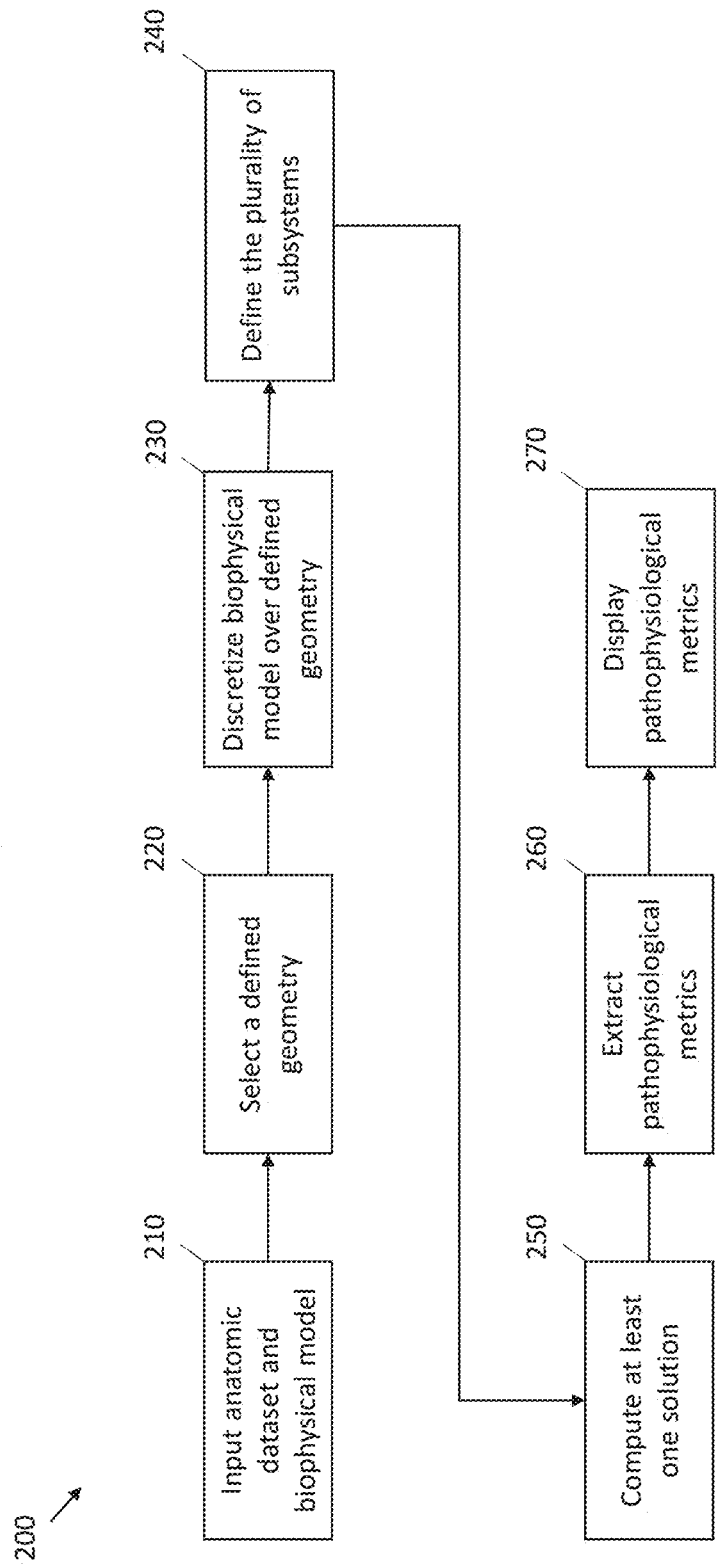
FIG. 5 depicts a schematic representation in block-diagram form of a method for simulating the pathophysiology of intervertebral discs in accordance with one embodiment of the present invention.

With reference to FIG. 5, depicted therein is a method 200 for applying the aforementioned components in the simulation of the pathophysiology of an intervertebral disc. As may be seen, such method 200 may first comprise the step of an input 210 of the anatomic dataset 10 and the biophysical model 30, to be stored on at least one memory. As previously stated, the anatomic dataset 10 may be input either automatically, through an interconnected device, such as a diagnostic imaging device, or manually through a user.

Conversely, the biophysical model 30 may be already stored on the memory for use in accordance with the anatomic dataset 10. Further, as previously stated, such anatomic dataset 10 and biophysical model 30 may be disposed in connection with a simulation program 20, which may also be stored on the memory, all of which may be disposed to be operated on by at least one processor, for the simulation thereof.

The following steps of a method 200 in accordance with at least one embodiment of the invention comprises the selection 220 of a defined geometry 64. As previously stated, the defined geometry 64 may comprise, for instance, a particular geometric area of an intervertebral disc 60 for which a particular simulation may be processed. Accordingly, such a defined geometry 64 may pertain, for illustrative purposes, to an entire intervertebral disc or, alternatively, to a cross-sectional layer of an entire intervertebral disc 60, as depicted by the mesh in FIG. 2. Conversely, such defined geometry may comprise only a portion of an intervertebral disc, such as a region pertaining solely to the annulus fibrosis 62, the nucleus pulposus 61, or the cartilaginous endplates 63. Thus, the selection 220 of the defined geometry 64 may serve to specify the type of simulation to be run in accordance with the method 200.

In accordance therewith, the method 200 may subsequently discretize 230 the biophysical model 30 over such defined geometry 64. As may be understood, such discretization step 230 serves to improve the efficiency of the method 200 by transferring the continuous functions of which the biophysical model 30 is comprised into discrete counterparts, thereby simplifying such functions and constraining the biophysical model 30 only to those functions appropriate for representing the defined geometry 64.

The next step of the method 200, in accordance with at least one embodiment of the present invention comprises defining 240 the plurality of subsystems of the biophysical model 30. As previously stated, such subsystems comprise the governing equations 31, the constitutive equations 32, the boundary conditions 33, the initial conditions 34, and the parameter values 35. Moreover, as previously stated, such subsystems may be altered by a user in a further attempt to constrain the simulation to a specified application, as will be discussed in greater detail hereafter.

For example, although the solid phase 65, the fluid phase 66, and the solute phase 67 may be adopted to represent intervertebral disc tissues in the biophysical model 30, any such phases may be disabled in the biophysical model 30 if the biophysical activities or biophysical fields associated therewith are not relevant to the user in performing a specific application of the method 200. One way to effectuate such disablement is to selectively exclude the governing equations 31 pertaining to the irrelevant phase. For example, because the cell viability in an engineered intervertebral disc may be predicted by solving the governing equations related to the solute phase 67 and the cells in the solid phase 65, such governing equations 31 may be selectively used and disposed within the defined geometry 64. Alternatively, a phase may also be disabled indirectly by adjusting certain parameter values 35 to make the contribution of such phase to the overall biophysical model 30 negligible. For example, the mechanical responses, or disc height, of an intervertebral disc 60 at the static state may be simulated by setting the parameter values 35 pertaining to fluid permeability and solute diffusivities to values much higher than their physiologically reasonable levels, thereby negating their impact on the biophysical model 30 as a whole. Accordingly, the computational time may be significantly reduced without affecting the computed mechanical responses of an intervertebral disc 60 at the static state.

One such manner in which the plurality of subsystems may be defined 240 particularly comprises the simulation of an intervertebral disc 60 at in vivo human conditions. Specifically, in vivo human conditions may be prescribed to an intervertebral disc 60 by defining 240 the plurality of subsystems to comprise specific boundary conditions 33 disposed to closely represent such in vivo human conditions. While alternative boundary conditions 33 are contemplated herein, at least one embodiment of the present invention may dispose the method 200 to simulate such in vivo human conditions by prescribing the boundary conditions 33 in the following manner.

First, where the first boundary condition 51 comprises a Neumann boundary condition and the second boundary condition 52 comprises a Dirichlet boundary condition, it may be understood the boundary conditions 33 for each phase may be selectively divided into such first boundary condition 51 and such second boundary condition 52, to be applied to the biophysical model 30 as a whole. Moreover, such boundary conditions 33 may be prescribed in accordance with the type of intervertebral disc at issue, whether native or engineered. Accordingly, for a native intervertebral disc, such first boundary condition 51 and second boundary condition 52 may be defined by the outer surface of the annulus fibrosis, and the interface between the cartilaginous endplates and the vertebra. Likewise, for an engineered intervertebral disc, the first boundary condition 51 and the second boundary condition 52 may be defined according to the culture conditions of such engineered intervertebral disc. Accordingly, the boundary conditions 33 for the solid phase 65, the fluid phase 66, and the solute phase 67 may be defined as follows, wherein n represents the outward unit normal to the boundary and * represents the prescribed values:

| Phase | First Boundary Condition (51) | Second Boundary Condition (52) |
|---|---|---|
| Solid phase/Mixture (65) | $\sigma \cdot n = \sigma^* \cdot n$ | $u = u^*$ |
| Fluid phase (66) | $j^w \cdot n = j^{w*} \cdot n$ | $\varepsilon^w = \varepsilon^{w*}$ |
| Solute phase (67) | $j^\alpha \cdot n = j^{\alpha*} \cdot n$ | $\varepsilon^\alpha = \varepsilon^{\alpha*}$ |

Accordingly, with such boundary conditions 33 in mind, the defining 240 of the boundary conditions 33 subsystem in relation to the remaining biophysical model 30 may comprise the appropriate application of certain boundary conditions 33, pertaining to specified portions of the biophysical model 30. Specifically, such boundary conditions 33 may comprise a first designated boundary condition 53, and second designated boundary condition 54, and a third boundary condition 55, each of which will be discussed in greater detail hereafter, with reference to FIG. 6.

The first designated boundary condition 53 may comprise the application of a first boundary condition 51, representing an equivalent spring boundary condition, to the outer surface of the annulus fibrosis, thereby representing the mechanical interaction between an intervertebral disc 60 and its surrounding tissues. If the mechanical interaction is not to be considered, it may be understood the parameter value 35 representing the equivalent spring stiffness for such first boundary condition 51 may be set to zero.

The second designated boundary condition 54 may comprise a selective application of either the first boundary condition 51 and the second boundary condition 52, dependent upon the type of mechanical loading at issue on the superior and/or inferior surface of an intervertebral disc 60. Specifically, the application of either the first boundary condition 51 or the second boundary condition 52 depends upon whether such mechanical loading on the superior and/or inferior surface of an intervertebral disc 60 is prescribed by displacements on the interface of the cartilaginous endplates 63 and the vertebra, or whether such mechanical loading may be described by mechanical force and/or stress. In the event such mechanical loading comprises displacements, then the second boundary condition 52 may be applied to such interfaces of the cartilaginous endplates 63 and the vertebra. Conversely, where such mechanical loading comprises mechanical force or stress, the full or partial superior and/or inferior vertebrae may be included within the biophysical model 30 and the first boundary condition 51 may be applied on the vertebra surfaces.

The third designated boundary condition 55 may comprise the selective application of the first boundary condition 51 and the second boundary condition 52 for the values of chemical potential and electro-chemical potential of an intervertebral disc 60 for the fluid phase 66 and the solute phase 67, respectively.

As may be understood, when defining 240 the plurality of subsystems, any deformed state may be chosen as a reference configuration for strain. However, the swelling pressure at such reference configuration should be subtracted from the total stress in the simulation. Likewise, one must note the computed mechanical stress is not an absolute value, but rather, is a relative value to such reference configuration.

With continued reference to FIG. 5, it may be seen the method 200 in accordance with at least one embodiment of the present invention may further comprise the step of computing 250 at least one solution to the biophysical model using the simulation program. As previously stated, such computation 250 may comprise the application of at least one of a plurality of numerical methods to determine the solutions to the biophysical model. In the event boundary conditions 33 have been applied in accordance with the aforementioned step for defining 240 the plurality of subsystems, it may be understood such at least one solution may be constrained to only those solutions which represent the simulation of an intervertebral disc 60 at in vivo human conditions. Finally, once such at least one solution has been determined, the pathophysiological metrics 40 may be extracted 260 therefrom, and subsequently displayed 270 using a graphic user interface.

With additional reference to FIG. 7, at least one embodiment of the present invention may further comprise a method 200 disposed to store 280 such extracted pathophysiological metrics 40 as historical data, thereby allowing for the subsequent comparison and display of pathophysiological metrics 40 obtained from subsequent simulations therewith.

Moreover, as may be seen with continued reference to FIG. 7, one additional step may be contemplated in at least one embodiment of the present invention, namely, a step for selectively redefining 240a the plurality of subsystems. As may be understood, such selective redefining 240a of the plurality of subsystems of the biophysical model 30 may allow a user to research a plurality of specified pathophysiological metrics 40 from a single anatomic dataset 10. Likewise, such selective redefining 240a may alternatively allow a user to generate specific degeneration scenarios of an intervertebral disc 60 stemming from a single anatomic dataset 10.

For instance, one such way the plurality of subsystems may be selectively redefined 240a is to simulate the disc degeneration of an intervertebral disc 60 at in vivo human conditions. More specifically, a user may selectively redefine 240a certain subsystems of the biophysical model 30 to generate specified conditions in which the degeneration of an intervertebral disc 60 at in vivo human conditions may occur, thereby allowing a user to model an intervertebral disc 60 at in vivo human conditions for an extended length of time, thus allowing for the realistic modeling thereof.

For example, while alternative methods and techniques for selectively redefining 240a the plurality of subsystems to represent the disc degeneration of an intervertebral disc 60 at in vivo human conditions are contemplated herein, at least one embodiment of the present invention may employ three alternative ways in which in vivo disc degeneration may be simulated through such selective redefinement 240a.

For instance, one such technique comprises changing the boundary conditions 33 to generate disc degeneration cascades in the simulated domain. For example, a user may progressively alter the boundary conditions 33 to reduce the solute electro-chemical potential at a boundary of an intervertebral disc 60, thereby simulating the effects of same over a period of time.

Likewise, an alternative technique comprises changing the constitutive equations 32 to change the material properties of certain aspects of an intervertebral disc 60. For instance, a user may reduce the permeability of an intervertebral disc 60 to obtain pathophysiological metrics 40 in accordance with FIG. 3. Further, a user may instead alter the spatial distribution of glycosaminoglycan content in a degenerated disc to obtain pathophysiological metrics 40 in accordance with FIG. 4.

Moreover, one further technique comprises changing the constitutive equations 32 to adjust the cell metabolic activities or viability thereof. For instance, a user may reduce the glycosaminoglycan synthesis rate to simulate the loss of glycosaminoglycan content in the degeneration process.

Of course, all pathophysiological metrics 40 obtained through such selective redefinement 240a of the plurality of subsystems may be stored 280 as historical data, for later comparison. In this manner, the degeneration of an intervertebral disc 60 at in vivo human conditions may be modeled for an extended length of time and at multi-scale levels, thereby allowing for a more accurate modeling thereof.

Accordingly, it may be understood the present invention provides a computer-implemented system for modeling the pathophysiology of human intervertebral discs. Moreover, in addition to providing the ability to model such intervertebral discs as a part of in vitro cell and in vitro explant models, at least one embodiment of the present invention further enables a user to model an intervertebral disc at in vivo human conditions, while minimizing and/or eliminating the typical limitations encountered when attempting to model an intervertebral disc under such conditions. For example, the ability of at least one embodiment of the present invention to both impose in vivo human conditions, and likewise simulate the degeneration of a single intervertebral disc over changing conditions may allow a user to model a human intervertebral disc at multi-scale levels while simultaneously investigating the chronic degradation process an intervertebral disc may experience. Finally, yet additional embodiments of the present invention may likewise allow a user to systematically synthesize existing experimental results to illustrate the pathophysiology of an intervertebral disc, obtain quantitative information on complicated bioinformatics interactions, and predict the evolution of intervertebral disc pathophysiology as caused by a plurality of external stimuli.

Since many modifications, variations, and changes in detail may be made to the described preferred embodiment of the present invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A method for simulating the pathophysiology of intervertebral discs, the method, to be performed by at least one processor disposed in connection with a memory, comprising:
   disposing an anatomic database and a biophysical model in connection with a simulation program, the biophysical model comprising a plurality of subsystems;
   selecting a defined geometry from the anatomic dataset;
   discretizing the biophysical model over the defined geometry;
   defining the plurality of subsystems to comprise boundary conditions configured to be progressively altered to generate disc degeneration cascades, said boundary conditions comprising a first boundary condition and a second boundary condition;
   defining the plurality of subsystems to further comprise constitutive equations configured to be selectively defined to change the material properties and cell metabolic activities of the intervertebral disc;
   selectively applying said first boundary condition and said second boundary condition to said biophysical model to simulate in vivo conditions, said first boundary condition comprising a Neumann boundary condition and said second boundary condition comprising a Dirichlet boundary condition, said first boundary condition and said second boundary condition each applied to a solid phase, fluid phase, and solute phase defined by said anatomic dataset such that:
      when said anatomic dataset defines a native intervertebral disc, said first boundary condition and said second boundary condition define the outer surface of the annulus fibrosis and the interface between the cartilaginous endplates and the vertebra;
      when said anatomic dataset defines an engineered intervertebral disc, said first boundary condition and said second boundary condition define the culture conditions;
   computing at least one solution using the simulation program;
   returning pathophysiological metrics according to the at least one solution; and
   displaying the pathophysiological metrics.

2. The method of claim 1, wherein the plurality of subsystems comprises governing equations, constitutive equations, initial conditions, and parameter values.

3. The method of claim 2, wherein the boundary conditions comprise a first boundary condition and a second boundary condition.

4. The method of claim 1, further comprising:
   displaying historical information alongside the pathophysiological metrics.

5. The method of claim 4, wherein the historical information comprises pathophysiological metrics of prior simulations.

6. The method of claim 1, wherein the defined geometry is selected from the group consisting of a whole intervertebral disc or a portion of an intervertebral disc, each disposed either in two-dimensional space or three-dimensional space.

7. The method of claim 1, wherein the simulation program comprises at least one algorithm disposed to determine the at least one solution.

8. The method of claim 1, wherein the at least one processor is disposed in input-output relation with a graphic user interface.

9. A system configured to model the pathophysiology of intervertebral discs at in vivo human conditions, said system comprising:
   a memory disposed to store an anatomic dataset, a biophysical model, and a simulation program;
   said biophysical model comprising boundary conditions, said boundary conditions comprising a first boundary condition and a second boundary condition;
   said biophysical model further comprising a plurality of subsystems, said plurality of subsystems comprising constitutive equations configured to be selectively defined to change the material properties and cell metabolic activities of the intervertebral disc;
   said memory disposed in connection with a processor, said processor disposed to:
      select a defined geometry from said anatomic dataset, said defined geometry comprising the intervertebral disc in a three-dimensional space;
      discretize said biophysical model over said defined geometry;
      selectively apply said first boundary condition and said second boundary condition to said biophysical model to simulate in vivo conditions, said first boundary condition comprising a Neumann boundary condition and said second boundary condition comprising a Dirichlet boundary condition, said first boundary condition and said second boundary condition each applied to a solid phase, fluid phase, and solute phase defined by said anatomic dataset such that:
         when said anatomic dataset defines a native intervertebral disc, said first boundary condition and said second boundary condition define the outer surface of the annulus fibrosis and the interface between the cartilaginous endplates and the vertebra;
         when said anatomic dataset defines an engineered intervertebral disc, said first boundary condition and said second boundary condition define the culture conditions;
      redefine at least one subsystem of said biophysical model to simulate in vivo conditions by applying at least one selective redefinement, said at least one selective redefinement comprising:
         a first selective change to least one of said first boundary condition and said second boundary condition to generate at least one disc degeneration cascade in the intervertebral disc;
         a second selective change to at least one of said constitutive equations to change the material properties of the intervertebral disc;
         a third selective change to at least one of said constitutive equations to change the cell metabolic activities of the intervertebral disc; and
      compute at least one solution using said simulation program.

10. The system of claim 9, wherein said processor is disposed for user input.

11. The system of claim 10, wherein said user input comprises an input of said anatomic dataset.

12. The system of claim 10, wherein said user input comprises changing said biophysical model.

13. The system of claim 10, wherein said user input comprises applying a first designated boundary condition, a second designated boundary condition, and a third designated boundary condition to said biophysical model, wherein:
   said first designated boundary condition comprises application of an equivalent spring boundary condition to the outer surface of the annulus fibrosis;
   said second designated boundary condition comprises application of said first boundary condition if the mechanical loading on the surface of the intervertebral disc comprises mechanical stress, or said second boundary condition if the mechanical loading on the surface of the intervertebral disc comprises displacements; and
   said third designated boundary condition comprising said first boundary condition for the chemical potential and electro-chemical potential of the fluid phase, and said second boundary condition for the chemical potential and electro-chemical potential of the solid phase.

14. The system of claim 10, wherein said biophysical model further comprises a plurality of subsystems.

15. The system of claim 9, wherein said processor is disposed in connection with a graphic user interface.

16. The system of claim 15, wherein said processor is disposed to extract pathophysiological metrics from said at least one solution and display said pathophysiological metrics on said graphic user interface.

17. The system of claim 9, wherein said first selective change comprises a reduction in the solute electro-chemical potential at a boundary of the intervertebral disc.

18. The system of claim 9, wherein said second selective change comprises a reduction in the permeability of the intervertebral disc.

19. The system of claim 9, wherein said second selective change comprises an alteration in the spatial distribution of glycosaminoglycan content in the intervertebral disc.

20. The system of claim 9, wherein said third selective change comprises a reduction in the glycosaminoglycan synthesis rate in the intervertebral disc.

* * * * *